(12) United States Patent
Suzuki

(10) Patent No.: US 10,555,843 B2
(45) Date of Patent: Feb. 11, 2020

(54) ABSORBENT ARTICLE

(71) Applicant: DAIO PAPER CORPORATION, Ehime (JP)

(72) Inventor: Yoko Suzuki, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 575 days.

(21) Appl. No.: 15/316,297

(22) PCT Filed: Jun. 11, 2015

(86) PCT No.: PCT/JP2015/066844
§ 371 (c)(1),
(2) Date: Dec. 5, 2016

(87) PCT Pub. No.: WO2015/190547
PCT Pub. Date: Dec. 17, 2015

(65) Prior Publication Data
US 2017/0172818 A1    Jun. 22, 2017

(30) Foreign Application Priority Data

Jun. 13, 2014  (JP) ................................ 2014-122037
Jun. 13, 2014  (JP) ................................ 2014-122044

(51) Int. Cl.
*A61F 13/15*    (2006.01)
*A61F 13/511*   (2006.01)
(Continued)

(52) U.S. Cl.
CPC ........ *A61F 13/51108* (2013.01); *A61F 13/15* (2013.01); *A61F 13/4704* (2013.01);
(Continued)

(58) Field of Classification Search
CPC .......................... A61F 13/51108; A61F 13/15;
A61F 13/4704; A61F 13/4751; A61F
13/4756; A61F 13/52; A61F 13/539
(Continued)

(56) References Cited

U.S. PATENT DOCUMENTS

2010/0178456 A1    7/2010  Kuroda et al.
2011/0130737 A1*   6/2011  Sagisaka ............. A61F 13/4704
                                                       604/380

(Continued)

FOREIGN PATENT DOCUMENTS

JP    H11-113955    4/1999
JP    2002-065741   3/2002
(Continued)

OTHER PUBLICATIONS

International Search Report dated Sep. 1, 2015.

*Primary Examiner* — Jacqueline F Stephens
(74) *Attorney, Agent, or Firm* — IPUSA, PLLC

(57) ABSTRACT

An absorbent article in which an absorbent body is provided between a liquid permeable topsheet and a backsheet, includes an absorbent body emboss provided from a front surface side of the absorbent body before stacking the liquid permeable topsheet to surround an area corresponding to a body fluid expelling portion; and a front surface emboss, formed separately from the absorbent body emboss and not to overlap the absorbent body emboss, provided from a front surface side of the liquid permeable topsheet.

14 Claims, 11 Drawing Sheets

(51) Int. Cl.
*A61F 13/539* (2006.01)
*A61F 13/47* (2006.01)
*A61F 13/475* (2006.01)
*A61F 13/51* (2006.01)

(52) U.S. Cl.
CPC ...... *A61F 13/4751* (2013.01); *A61F 13/4756* (2013.01); *A61F 13/4758* (2013.01); *A61F 13/52* (2013.01); *A61F 13/539* (2013.01)

(58) Field of Classification Search
USPC .......................... 604/378, 379, 380, 385.101
See application file for complete search history.

(56) References Cited

U.S. PATENT DOCUMENTS

| | | | | |
|---|---|---|---|---|
| 2011/0251575 A1* | 10/2011 | Kuroda | ............... | A61F 13/4704 604/380 |
| 2013/0165885 A1* | 6/2013 | Kurihara | ............. | A61F 13/4756 604/380 |

FOREIGN PATENT DOCUMENTS

| | | |
|---|---|---|
| JP | 2005-073921 | 3/2005 |
| JP | 2005-160702 | 6/2005 |
| JP | 2006-014792 | 1/2006 |
| JP | 2007-089819 | 4/2007 |
| JP | 2009-000351 | 1/2009 |
| JP | 2011-234896 | 11/2011 |
| JP | 2012-143535 | 8/2012 |
| WO | 2008/146541 | 12/2008 |

* cited by examiner (A) ABSORBENT BODY EMBOSS

FRONT SURFACE EMBOSS (B) FRONT SURFACE EMBOSS

FRONT SURFACE EMBOSS (C) ABSORBENT BODY EMBOSS FRONT SURFACE EMBOSS

FIG.12

(A) WEAK STRONG (B) UNIFORM
25    27

FIG.13

| | EXAMPLE 1 | EXAMPLE 2 |
|---|---|---|
| PATTERN | 25, 2mm, 27 | 25, 3mm, 27 |
| BLOCKINGS OF PATTERN | ○(NONE) | ○(NONE) |
| SPLITS | ○(NONE) | ○(NONE) |
| COMPRESSION DEGREE (UNIFORMITY) | ○ | ○ |
| COMPRESSION DEGREE (THICKNESS) | ○ | ○ |
| RUNNABILITY (TOTAL) | ○ | ○ |
| DIFFUSION PREVENTION ABILITY | ◎ | ○ |
| HARDNESS WHEN WEARING | ○ | ○ |

FIG.14

| | COMPARATIVE EXAMPLE 1 | COMPARATIVE EXAMPLE 2 | COMPARATIVE EXAMPLE 3 |
|---|---|---|---|
| PATTERN | 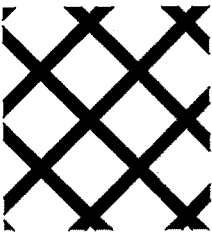 | 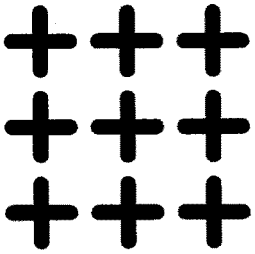 | 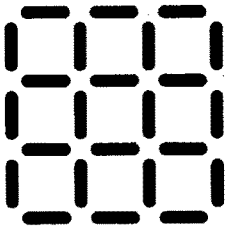 |
| BLOCKINGS OF PATTERN | ×(OCCUR) | ×(OCCUR) | ○(NONE) |
| SPLITS | ×(OCCUR) | △ | ○(NONE) |
| COMPRESSION DEGREE (UNIFORMITY) | ○ | × | × |
| COMPRESSION DEGREE (THICKNESS) | ○ | × | × |
| RUNNABILITY (TOTAL) | × | × | × |
| DIFFUSION PREVENTION ABILITY | ◎ | ○ | ○ |
| HARDNESS WHEN WEARING | ○ | ○ | ○ |

FIG.15

| | COMPARATIVE EXAMPLE 4 | COMPARATIVE EXAMPLE 5 | COMPARATIVE EXAMPLE 6 |
|---|---|---|---|
| PATTERN | 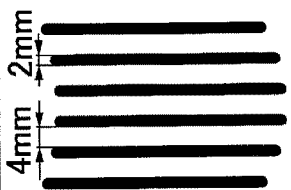 | 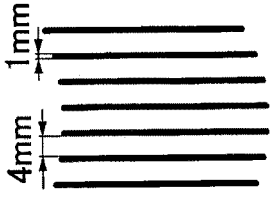 | 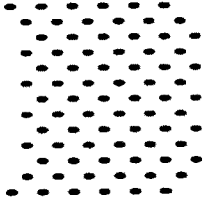 |
| BLOCKINGS OF PATTERN | ○(NONE) | ○(NONE) | ○(NONE) |
| SPLITS | ○(NONE) | ○(NONE) | ○(NONE) |
| COMPRESSION DEGREE (UNIFORMITY) | ○ | ○ | ○ |
| COMPRESSION DEGREE (THICKNESS) | ○ | ○ | × |
| RUNNABILITY (TOTAL) | ○ | ○ | △ |
| DIFFUSION PREVENTION ABILITY | ○ | ○ | × |
| HARDNESS WHEN WEARING | × | × | ○ |

ABSORBENT ARTICLE

BACKGROUND OF THE INVENTION

1. Field of the Invention

The present invention mainly relates to an absorbent article used in incontinence pads, sanitary napkins, panty liners, medical pads, toiletries, disposal diapers and the like, and relates to an absorbent article in which an absorbent body emboss is provided from a front surface of an absorbent body before stacking a liquid permeable topsheet, and a front surface emboss is provided from a front surface of the liquid permeable topsheet. Further, the present invention relates to an absorbent article including a lattice-shaped emboss in which the emboss is provided in a lattice-shaped pattern.

2. Description of the Related Art

Conventionally, an absorbent article is known in which an absorbent body is provided between a liquid impermeable backsheet, such as a polyethylene sheet or a non-woven fabric made of laminated polyethylene sheets, and a liquid permeable topsheet, such as a non-woven fabric or a permeable plastic sheet.

This kind of absorbent article has been improved many times, and various means are provided in order to prevent leakage of body fluid. As one of the means to prevent leakage of body fluid, a technique is provided to form a concave groove by heat embossing. For example, in the following Patent Document 1, an absorbent article is disclosed in which an elongated annular leakproof groove, in which a center portion in a longitudinal direction is constricted, is provided around a center portion of the absorbent article to integrate a front surface layer and an absorbent layer.

Further, in the following Patent Document 2, an absorbent article is disclosed which includes, in addition to a front surface emboss that is provided from a front surface of a liquid permeable topsheet, an absorbent body emboss provided to an absorbent body at a providing area of the front surface emboss before stacking the liquid permeable topsheet.

Meanwhile, various absorbent articles are provided in which embosses with various patterns are provided for preventing body fluid absorbed in an absorbent body from leaking from an end portion after diffusing inside the absorbent body, and for blocking the body fluid that flows at a surface to be absorbed and retained in the absorbent body. As one of the emboss patterns, a lattice-shaped emboss is known in which the emboss is provided in a lattice-shape in a plane view. The lattice-shaped emboss has merits such as a good blocking effect for the body fluid, and a good fittability because hardness caused by the compression is lessened as compressed portions and non-compressed portions are alternatively formed.

For example, in the following Patent Document 3, an absorbent article is disclosed in which a plurality of longitudinal emboss concave portions are formed in an absorbent body to extend from a substantially center portion in a longitudinal direction of the absorbent body to a ventral portion and a dorsal portion at both end sides in the longitudinal direction of the absorbent body, with a predetermined space in a width direction. Further, diffusion emboss concave portions that diffuse body fluid widely to the ventral portion and the dorsal portion, respectively, are formed at the ventral portion and the dorsal portion at both end sides of the longitudinal emboss concave portions. The diffusion emboss concave portions are formed as rhombic lattice-shaped emboss concave portions that are inclined with respect to the longitudinal direction of the absorbent body.

Further, in the following Patent Document 4, an absorbent body is disclosed in which concave portions that extend in an inclined direction with respect to a longitudinal direction are formed at both ends of a middle portion in the longitudinal direction.

PATENT DOCUMENTS

Patent Document 1: Japanese Patent No. 3,781,617
Patent Document 2: Japanese Laid-open Patent Publication No. 2005-160702
Patent Document 3: Japanese Patent No. 4,008,868
Patent Document 4: Japanese Laid-open Patent Publication No. 2012-143535

However, for the leakproof groove as disclosed in the above described Patent Document 1 in which an annular closed emboss line is provided, embossing is performed by compression from a front surface of the front surface sheet at once. In such a case, a large change of compression directions or a difference in a compressed degree occurs at a boundary portion between a feed direction of a manufacturing line (MD direction) and a perpendicular direction (CD direction). Thus, there are problems such as wrinkles or twists are generated so that the compression is not properly performed because distortion of compressive force applied to the front sheet is accumulated, and runnability is worsened because a product twists around an emboss roller as emboss portions bite emboss protruding portions of the emboss roller.

Further, the absorbent article as disclosed in the above described Patent Document 2 includes an embodiment in which the front surface emboss having a dot pattern is formed to overlap the linear absorbent body emboss. In such a case, a user may feel hardness of a product at a portion where the front surface emboss and the absorbent body emboss overlap to feel uncomfortable when wearing the absorbent article.

Further, for the lattice-shaped emboss disclosed in Patent Document 3 or 4, the emboss groove is formed to cross at intersections of strips of the lattice. Thus, there are no escapeways to disperse pressure when compressed by an emboss roller in manufacturing steps, and wrinkles of a front surface material, distortion of the emboss groove or the like are easily generated. Further, with this, there is a problem such as runnability in embossing is worsened because a product twists around an emboss roller as emboss portions of the product bite emboss protruding portions of the emboss roller, blocking occurs as paper powders are accumulated at corner portions of crossing portions of the emboss roller, or the like.

Further, although a blocking effect of the body fluid is good at crossing portions of the emboss groove of the lattice-shaped emboss, with this, the body fluid is completely terminated from diffusing outward. Thus, there is a problem such as absorbing volume of the absorbent body in total is lowered as the body fluid tends to be accumulated at inner sides of the crossing portions.

Here, if the lattice-shaped emboss is a square lattice in which strips of the lattice are provided to extend along the longitudinal direction and the width direction of the absorbent article, and a line transferring direction (MD direction) in manufacturing steps is the same as the longitudinal direction of the absorbent article, a difference in linear pressure in compression by an emboss roller becomes large such as the linear pressure becomes high at a portion where an emboss groove that extends along the width direction of the absorbent article is formed, while the linear pressure becomes low at a portion where only an emboss groove that extends along the longitudinal direction is formed. Thus, splits, wrinkles, twists or the like of the front surface material are easily generated. Further, if the lattice is placed as the square lattice, a user may feel hardness when wearing the absorbent article because it is difficult for the absorbent article to deform due to stiffness of the emboss groove when the absorbent article is deformed along curves in front and rear directions and in a width direction of a body.

SUMMARY OF THE INVENTION

The main problem to be solved by the present invention is to provide an absorbent article in which generation of wrinkles or twists in embossing is prevented, runnability of the embossing is improved, hardness due to the embossing is lowered, uncomfortable feeling when being worn is reduced and a diffusion preventing effect of body fluid is increased.

As the invention of claim 1 to solve the above problem, there is provided an absorbent article in which an absorbent body is provided between a liquid permeable topsheet and a backsheet, including an absorbent body emboss provided from a front surface side of the absorbent body before stacking the liquid permeable topsheet to surround an area corresponding to a body fluid expelling portion; and a front surface emboss, formed separately from the absorbent body emboss and not to overlap the absorbent body emboss, provided from a front surface side of the liquid permeable topsheet.

According to the above invention of claim 1, an absorbent body emboss is provided from a front surface side of the absorbent body before stacking the liquid permeable topsheet to surround an area corresponding to a body fluid expelling portion; and a front surface emboss, formed separately from the absorbent body emboss and not to overlap the absorbent body emboss, is provided from a front surface side of the liquid permeable topsheet. The absorbent body emboss is provided in order to prevent body fluid absorbed in the absorbent body from diffusing inside the absorbent body and leaking from an end portion of the absorbent body. Meanwhile, the front surface emboss is provided in order to prevent the body fluid in the absorbent body from diffusing and to prevent the body fluid that flows along a groove of a body such as a body fluid expelling portion or the like from flowing at a front surface of the liquid permeable topsheet to leak.

At this time, different from the conventional absorbent article in which the closed emboss line that surrounds the area corresponding to the body fluid expelling portion is formed from a front surface of the absorbent body or a front surface of the liquid permeable topsheet by embossing at once, according to the absorbent article of the invention, the absorbent body emboss and the front surface emboss are provided separately not to overlap with each other. Thus, force applied to a material in embossing is dispersed, and generation of wrinkles, twists or the like in the absorbent body and the front sheet. As a result, according to the absorbent article of the invention, the emboss can be properly processed, twisting around the emboss roller in embossing does not occur, and runnability becomes stable.

Further, as the absorbent body emboss and the front surface emboss are formed separately not to overlap with each other, compared with a case when the front surface emboss is provided to overlap the absorbent body emboss, hardness of the emboss can be prevented, and worsening of fittability due to the hardness of the emboss can be prevented.

As the invention of claim 2, there is provided the absorbent article according to claim 1, wherein the absorbent body emboss includes linear absorbent body embosses, provided at both sides of the area corresponding to the body fluid expelling portion in a width direction, respectively, each extending along a longitudinal direction of the absorbent article, and wherein the front surface emboss is formed by curved lines, provided at front and rear portions of the area corresponding to the body fluid expelling portion in the longitudinal direction, respectively, each extending along the width direction of the absorbent article while bulging outwardly in the longitudinal direction.

According to the above invention of claim 2, by providing the absorbent body emboss to include linear absorbent body embosses, provided at both sides of the area corresponding to the body fluid expelling portion in a width direction, respectively, the body fluid absorbed in the absorbent body is prevented from diffusing in the width direction and leaking from end portions of the absorbent body in the width direction at both sides of the body fluid expelling portion in the width direction. Further, by forming the front surface emboss by curved lines, provided at front and rear portions of the area corresponding to the body fluid expelling portion in the longitudinal direction, respectively, each extending along the width direction of the absorbent article while bulging outwardly in the longitudinal direction, the body fluid that flows along the groove of the body is blocked by the front surface emboss to be absorbed and retained in the absorbent body, and prevented from leaking from end portions at the front and rear portions of the body fluid expelling portion.

As the invention of claim 3, there is provided the absorbent article according to claim 1, wherein the absorbent body emboss and the front surface emboss are connected with each other, or provided in the vicinity with each other.

According to the above invention of claim 3, by providing the absorbent body emboss and the front surface emboss to be connected with each other, or in the vicinity with each other, the body fluid is prevented from leaking from a space between the absorbent body emboss and the front surface emboss.

As the invention of claim 4, there is provided the absorbent article according to claim 1, wherein the front surface emboss is provided at each of front and rear portions of the area corresponding to the body fluid expelling portion in the longitudinal direction, respectively, as a single emboss extending along the width direction, or a plurality of embosses, each extending along the width direction, with a space therebetween in the longitudinal direction.

According to the above invention of claim 4, by providing the front surface emboss to include a plurality of embosses, leakage from an end portion in the longitudinal direction can be surely prevented.

As the invention of claim 5, there is provided the absorbent article according to claim 1, wherein the absorbent body emboss includes lattice-shaped absorbent body embosses, provided at front and rear portions of the area corresponding to the body fluid expelling portion in the longitudinal direction, respectively, each formed at an area extending along the width direction of the absorbent article.

According to the above invention of claim 5, absorbent body emboss is provided to include lattice-shaped absorbent body embosses, provided at front and rear portions of the area corresponding to the body fluid expelling portion in the longitudinal direction, respectively, each formed at an area extending along the width direction of the absorbent article, the body fluid that diffuses in the absorbent body in the width direction and the longitudinal direction is blocked by the linear or the lattice-shaped absorbent body emboss, and leakage of the body fluid from end portions of the absorbent body can be surely prevented.

As the invention of claim 6, there is provided the absorbent article according to claim 1, wherein the front surface emboss includes lattice-shaped front surface embosses, provided at front and rear portions of the area corresponding to the body fluid expelling portion in the longitudinal direction, respectively, each formed at an area extending along the width direction of the absorbent article.

As the invention of claim 7, there is provided the absorbent article according to claim 5 or 6, wherein each of the lattice-shaped absorbent body embosses or each of the lattice-shaped front surface embosses is provided with intermittent portions at which emboss grooves are placed intermittently at crossing portions of strips of the respective lattice-shaped absorbent body, and is formed in a rhombic lattice-shape in which strips of the respective lattice-shaped absorbent body is inclined with respect to the longitudinal direction and the width direction of the absorbent article.

According to the above invention of claim 7, in the absorbent article including the lattice-shaped absorbent body emboss or the lattice-shaped front surface emboss, each of the lattice-shaped absorbent body embosses or each of the lattice-shaped front surface embosses is provided with intermittent portions at which emboss grooves are placed intermittently at crossing portions of strips of the respective lattice-shaped absorbent body so that the emboss groove is divided by the intermittent portions. Thus, pressure applied to the front surface material when compressing by the emboss roller in manufacturing steps is dispersed by the intermittent portions, and wrinkles of the front surface material, distortion of the emboss groove or the like are not generated. Therefore, twisting of a product around the emboss roller because the emboss groove bite the emboss roller can be prevented. Further, as crossing portions are not formed in the emboss groove, a problem such as paper powders are blocked at corner portions of the crossing portions can be solved and runnability of embossing becomes good.

Further, in the lattice-shaped absorbent body emboss or the lattice-shaped front surface emboss, the blocking effect of the body fluid can be obtained at each of strips of the lattice while a part of the body fluid blocked by the strips can diffuse outward because the emboss groove is placed intermittently at the intermittent portions. Thus, the body fluid can be absorbed and retained in a large range of the absorbent body so that the absorbing volume of the body fluid can be improved while maintaining the diffusion preventing effect of the body fluid.

Further, in the absorbent article of the invention, the lattice-shaped absorbent body emboss or the lattice-shaped front surface emboss is formed in a rhombic lattice-shape in which strips of the respective lattice-shaped absorbent body is inclined with respect to the longitudinal direction and the width direction of the absorbent article. Thus, the emboss groove is formed at a same ratio with respect to the line transferring direction, and linear pressure in emboss compression becomes substantially uniform. Therefore, splits, wrinkles, twists or the like of the front surface material can be prevented. Further, even when the absorbent article is deformed along curves in front and rear directions and in a width direction of a body, the strips of the lattice are not formed in a direction parallel to these directions. Thus, the absorbent article is prevented from hardly deforming due to stiffness of the lattice, and a user may not feel hardness when wearing the absorbent article.

As the invention of claim 8, there is provided the absorbent article according to claim 7, wherein the length of each of the intermittent portions is 2 to 5 mm.

According to the above invention of claim 8, by setting the length of each of the intermittent portions, at which the emboss groove is placed intermittently at the crossing portions of the lattice, to be 2 to 5 mm, the pressure can be appropriately dispersed in embossing, and the body fluid can be appropriately diffused outward without reducing the blocking effect of the body fluid.

As the invention of claim 9, there is provided the absorbent article according to claim 5 or 6, wherein a concave groove is provided at a skin contacting surface at the area corresponding to the body fluid expelling portion along the longitudinal direction, and wherein the lattice-shaped absorbent body embosses or the lattice-shaped front surface embosses are provided at front and rear areas of the concave groove, respectively.

According to the above invention of claim 9, by forming the concave groove at the area corresponding to the body fluid expelling portion, a large amount of the body fluid that is expelled at once can be instantly received to be temporarily reserved in the concave groove, and thus, the body fluid can be easily absorbed and retained in the absorbent body.

As described above in detail, according to the present invention, it is possible to prevent generation of wrinkles or twists in embossing, improve runnability of the embossing, lower hardness due to the embossing, reduce uncomfortable feeling when being worn and increase a diffusion preventing effect of body fluid.

BRIEF DESCRIPTION OF THE DRAWINGS

FIG. 12-(A) is an enlarged plan view of the conventional lattice-shaped emboss, and FIG. 12-(B) is an enlarged plan view of the lattice-shaped absorbent body emboss 25 of the invention;

FIG. 13 is a view (No. 1) in which performances by emboss patterns are compared;

FIG. 14 is a view (No. 2) in which performances by emboss patterns are compared; and FIG. 15 is a view (No. 3) in which performances by emboss patterns are compared.

DETAILED DESCRIPTION OF THE PREFERRED EMBODIMENTS

Next, embodiments of the present invention will be described below with reference to drawings.

(Basic Structure of Incontinence Pad 1)

Figure 1:
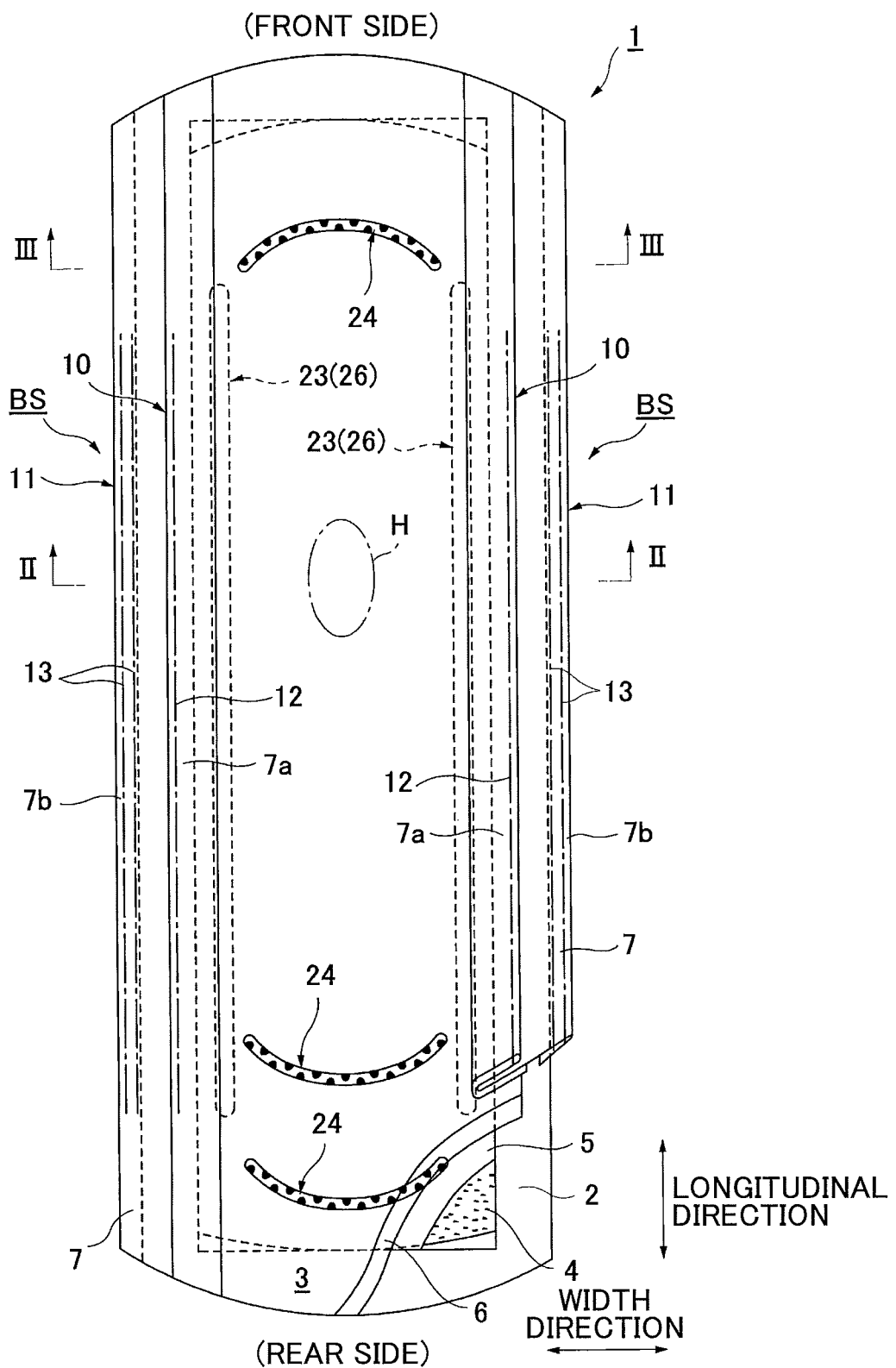
FIG. 1 is a partially broken developed view of an incontinence pad 1 of the invention.
Figure 2:
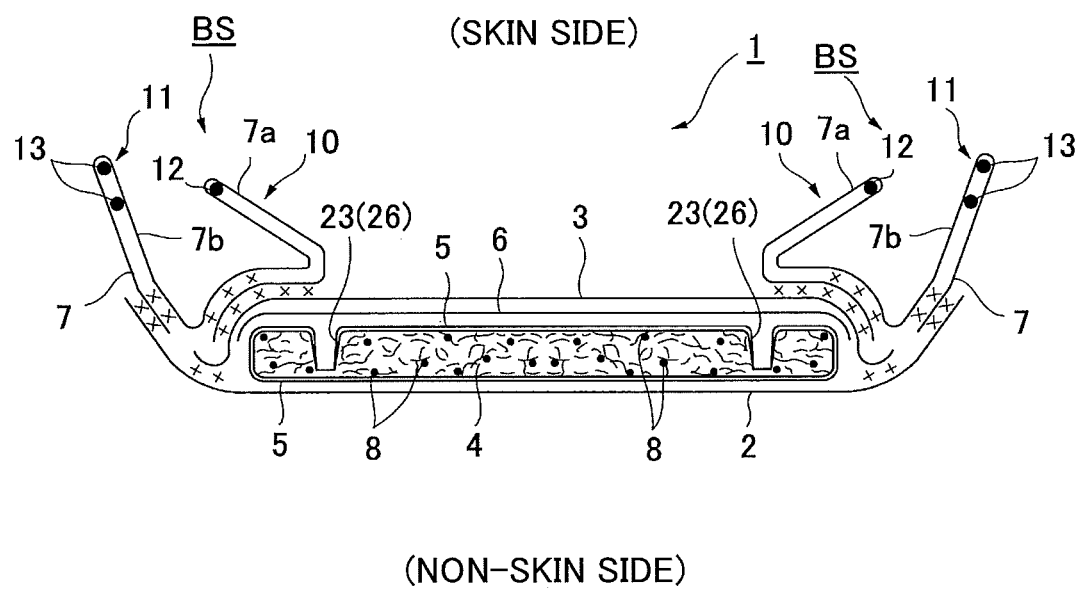
FIG. 2 is a cross-sectional view taken along a II-II line of FIG. 1.
Figure 3:
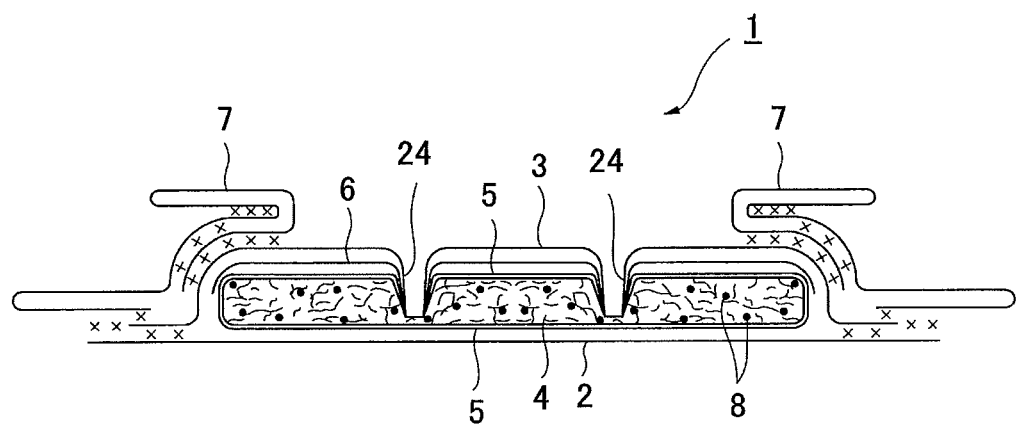
FIG. 3 is a cross-sectional view taken along a III-III line of FIG. 1.

As illustrated in FIG. 1 to FIG. 3, an incontinence pad 1 of the present invention is mainly constituted of a liquid impermeable backsheet 2 made of polyethylene, a liquid permeable topsheet 3 that allows urine and the like to rapidly permeate, an absorbent body 4 made of cotton-like pulp, synthetic pulp, or the like, and that is provided between both the sheets 2 and 3, an encapsulating sheet 5 made of a crepe paper sheet, a non-woven fabric or the like that surrounds the absorbent body to retain a shape and to improve diffusivity of the absorbent body 4, a hydrophilic second sheet 6 disposed between the liquid permeable topsheet 3 and the absorbent body 4, as necessary, and side non-woven fabrics 7 forming a matched pair of standing gathers BS that protrude toward a skin side in a predetermined zone including at least a body fluid expelling portion H in the longitudinal direction, while standing from approximately side edge parts of the absorbent body 4. Around the absorbent body 4, the outer end portions of the liquid impermeable backsheet 2 and the liquid permeable topsheet 3 are bonded with an adhesive such as a hot-melt adhesive or an adhesive means such as a heat seal and the like at end portions in the longitudinal direction, and the liquid impermeable backsheet 2 laterally protruding from the absorbent body 4 and the side non-woven fabrics 7 are bonded with the adhesive such as the hot-melt adhesive or the adhesive means such as the heat seal and the like at the edge portions on both sides.

Hereinafter, the structure of the incontinence pad 1 is further described in more detail. A sheet material having at least water shielding properties such as polyethylene, polypropylene or the like is used in the liquid impermeable backsheet 2. In addition to this, a non-woven fabric sheet can be also used after ensuring substantial impermeability by providing a waterproof film to cover the non-woven fabric sheet (in this case, the liquid impermeable backsheet is composed of the waterproof film and the non-woven fabric sheet). In recent years, a material having moisture permeability is often preferably used to prevent sweating. A microporous sheet obtained by forming a sheet by melting and kneading inorganic filler in olefin series resin such as polyethylene and polypropylene and then extruding the sheet in one axial direction or two axial directions, is preferably used as the waterproof and moisture permeable sheet material.

Next, a perforated or imperforate non-woven fabric or a porous plastic sheet is preferably used as the liquid permeable topsheet 3. For example, a regenerated fiber such as rayon and cupra, and a natural fiber such as cotton, can be used as a material fiber forming the non-woven fabric in addition to a synthetic fiber including an olefin series such as polyethylene and polypropylene, a polyester series, a polyamide series and the like. As the non-woven fabric, a non-woven fabric obtained by a proper processing method such as a spun lace method, a spun bond method, a thermal bond method, a melt blown method, and a needle punch method, can be used. Among the processing methods, the spun lace method is superior in terms of great flexibility and drape properties, and the thermal bond method is superior in terms of bulkiness and softness.

The absorbent body 4 is, for example, constituted of an absorbable fiber such as a fluff pulp and superabsorbent polymers 8, and is formed into an approximately oval shape extending long in a longitudinal direction of the pad in a planar shape in the illustrated example. The superabsorbent polymers 8 are, for example, formed into granular powders, and are diffused and mixed into the pulp forming the absorbent body 4.

Chemical pulp obtained from wood, a cellulose fiber such as dissolving pulp, and an artificial cellulose fiber such as rayon and acetate, are cited as examples available for the pulp, and softwood pulp having a fiber length longer than that of hardwood pulp is preferably used in terms of function and price. In this incontinence pad 1, as the absorbent body 4 is surrounded by the encapsulating sheet 5, as a result, the encapsulating sheet 5 is provided between the liquid permeable topsheet 3 and the absorbent body 4. Thus, an encapsulating sheet 5 having excellent absorbability serves to rapidly distribute the body fluid and to prevent urine and the like from flowing back. The fabric weight per unit area of the pulp is preferably set in a range of 100 g/m$^2$ to 600 g/m$^2$, and further preferably set in a range of 200 g/m$^2$ to 500 g/m$^2$.

For example, a cross-linking polyacrylate, a self-cross-linking polyacrylate, a saponified substance of a cross-linking copolymer of acrylic acid ester and vinyl acetate, a cross-linking substance of a copolymer of isobutylene and maleic anhydride, a cross-linking polysulfonate, and a partially cross-linking substance of a water swellable polymer such as polyethylene oxide and polyacrylamide are cited as examples of the superabsorbent polymer 8. Among the examples, a substance of acryl acid or an acrylate-based substance having a large amount of water absorption and a high absorption speed is preferable. The water-absorbing ratio (water-absorbency) and the absorption speed of the superabsorbent polymer having the above-mentioned water absorption performance can be adjusted by adjusting the cross-linking density and the cross-linking density gradient in its manufacturing process.

Moreover, a synthetic fiber may be mixed into the absorbent body 4. For example, a polyolefin series such as polyethylene or polypropylene, a polyester series such as polyethylene terephthalate and polybutylene terephthalate, and a polyamide series such as nylon, and a copolymer thereof, or a mixture of two kinds thereof, can be used as the synthetic fiber. Furthermore, a composite fiber such as a core-clad type fiber including a core made of a fiber with a high melting point and a clad made of a fiber with a low melting point, a side-by-side type fiber, and a division type, can be also used. When the synthetic fiber is made of a hydrophobic fiber, it is preferable to treat a surface of the synthetic fiber with a hydrophilic agent so as to have hydrophilic properties to the body fluid.

A paper material such as a tissue or the like, or a liquid permeable sheet such as a non-woven fabric or the like may be used as the encapsulating sheet 5. In particular, it is preferable to use the non-woven fabric for which damage (split) to a material hardly occurs. When the non-woven fabric is used, a non-woven fabric processed by a spun bond method or an SMS method, in particular, a non-woven fabric processed by the SMS method, is preferable as it has a good balance between the thin thickness and the strength. Here, for the encapsulating sheet 5, as long as a surface at a skin contacting surface (front surface) of the absorbent body 4 is not water repellency, its hydrophilic degree is not specifically limited.

The second sheet 6 just has to have hydrophilic properties to the body fluid. More specifically, a hydrophilic material that has hydrophilic properties in itself can be used as the second sheet 6 by using the regenerated fiber such as rayon and cupra, and the natural fiber such as cotton. Otherwise, a fiber treated to have the hydrophilic properties by treating a surface of a synthetic fiber including an olefin series such as polyethylene and polypropylene, a polyester series, a polyamide series and the like with a hydrophilic agent, can be used. In addition, the second sheet 6 may include a porous film layer on its rear side (the absorbent body 4 side) to provide tension, and may be made of a material including pulp.

On both sides of the top surface side of the present incontinence pad 1, side non-woven fabrics 7 are respectively provided along the longitudinal direction over the entire length of the incontinence pad 1, and outer parts of the side non-woven fabrics 7 extend laterally while the liquid impermeable backsheet 2 extends laterally. Side flaps are formed by attaching the laterally extended side non-woven fabric 7 parts to the laterally extended liquid impermeable backsheet 2 parts with the hot-melt adhesive and the like.

Either water-repellent non-woven fabric or hydrophilic non-woven fabric is used as the side non-woven fabric 7 depending on the desired function. For example, when regarding a function of preventing urine and the like from permeating or of improving a texture as important, it is preferable to use the water-repellent non-woven fabric such as SSMS, SMS or SMMS coated with water-repellent agent and the like of a silicon series, a paraffin series and an alkyl chromic chloride series. When regarding the absorbability of the body fluid as important, it is preferable to use a hydrophilic non-woven fabric obtained by making a swellable or porous synthetic fiber by a method of polymerizing the synthetic fiber in the presence of a compound having a hydrophilic group, for example, an oxidation product of polyethylene glycol, in the manufacture of the synthetic fiber, or a method of treating the surface with a metallic salt such as stannic chloride to partially dissolve the surface to form a porous surface and then to precipitate a metallic hydroxide on the surface, and then providing the hydrophilic property for the synthetic fiber by using capillary action. A fiber obtained by processing the natural fiber, the synthetic fiber or the regenerated fiber by a proper processing method is available for the side non-woven fabric 7.

The side non-woven fabrics 7 are properly folded to form the standing gathers BS of a double structure including the matched pair of inner standing gathers 10, 10 standing from the neighborhood of the edges of the absorbent body 4 toward the skin side, and the matched pair of outer standing gathers 11 that are located outside the inner standing gathers 10, constituted of the liquid impermeable backsheet 2 extending laterally so as to protrude from the absorbent body 4 and the side non-woven fabrics 7, and formed so as to stand toward the skin side. Here, the standing gather BS may have a single gather structure constituted of only one of the inner standing gather 10 or the outer standing gather 11, or may not be formed into a standing gather shape standing toward the skin side by just providing the side non-woven fabric 7 without raising it.

The structure of the inner standing gather 10 and the outer standing gather 11 is described below in more detail. As illustrated in FIG. 2, double sheet parts 7a, 7b are respectively formed on the inner side and the outer side in the width direction by folding both sides of the side non-woven fabric 7 in the width direction. At least one, in the illustrative example, one threadlike elastic stretchable member 12 is fixed at both ends or proper locations in the longitudinal direction, and is provided inside the double sheet part 7a. At least one, in the illustrative example, two threadlike elastic stretchable members 13 are fixed at both ends or proper locations in the longitudinal direction, and are provided inside the double sheet part 7b. By attaching the base edge portion of the double sheet part 7a on the inner side in the width direction to the upper surface of the liquid permeable topsheet 3 provided on a side portion of the absorbent body 4 with a hot-melt adhesive or the like, and attaching the base edge portion of the double sheet part 7b on the outer side in the width direction to the side edge portion of the liquid impermeable backsheet 2 laterally protruding from the absorbent body 4 with the hot-melt adhesive, the inner standing gather 10 standing toward the skin side is formed of the double sheet part 7a on the inner side in the width direction, and the outer standing gather 11 standing toward the skin side is formed of the double sheet part 7b on the outer side in the width direction. Here, as illustrated in FIG. 1, the side non-woven fabric 7 does not include the threadlike elastic stretchable members 12, 13 at the end portions in the longitudinal direction, and the double sheet part 7a on the inner side in the width direction is attached to the absorbent body 4 with a hot-melt adhesive.

(Absorbent Body Emboss 23 and Front Surface Emboss 24)

In the incontinence pad 1, an absorbent body emboss 23 that is provided from a front surface (skin surface) of the absorbent body 4 before stacking the liquid permeable topsheet 3 to surround the area corresponding to the body fluid expelling portion H, and a front surface emboss 24, separately formed from the absorbent body emboss 23 and not to overlap the absorbent body emboss 23, that is provided from a front surface side of the liquid permeable topsheet 3 are provided. The area corresponding to the body fluid expelling portion H is an area that contacts an urine expelling portion of a human body when a user wears the incontinence pad 1 at a normal state, and for a normal incontinence pad, the area is positioned at a center portion in the width direction and at a center portion in the longitudinal direction or a slightly front side of the center in the longitudinal direction.

Figure 4:
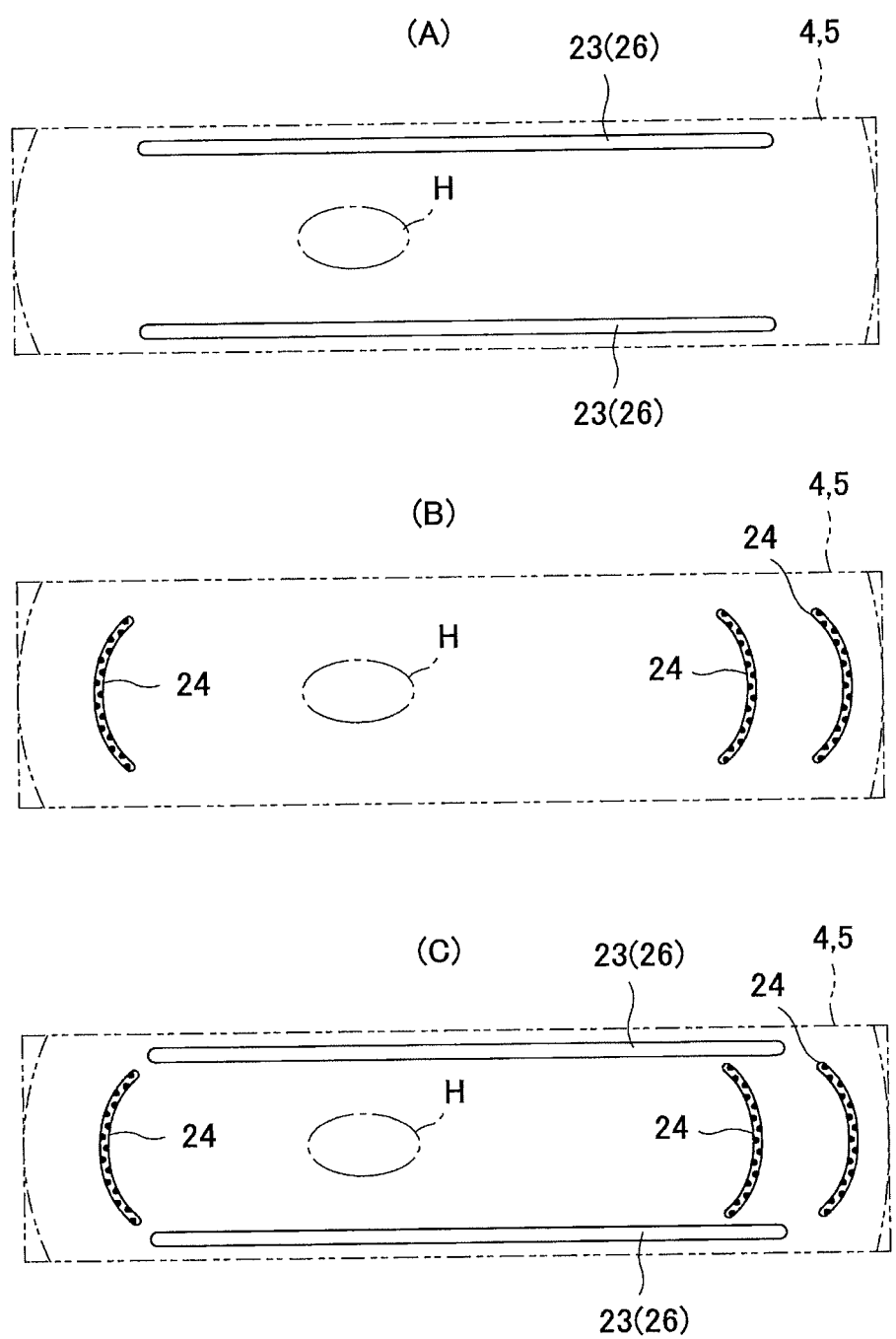
FIG. 4-(A) is a plan view of an absorbent body emboss 23, FIG. 4-(B) is a plan view of a front surface emboss 24 and FIG. 4-(C) is a plan view in which these are overlapped.

The absorbent body emboss 23 is an emboss that is provided from the front surface (skin surface) of the absorbent body 4 or the encapsulating sheet 5 that encapsulates the absorbent body 4 before stacking the liquid permeable topsheet 3. This means, as illustrated in FIG. 4-(A), the absorbent body emboss 23 is provided by compression from the front surface of the absorbent body 4 or the encapsulating sheet 5 when manufacturing the incontinence pad 1. The absorbent body emboss 23 is provided to block the body fluid absorbed in the absorbent body 4 from diffusing in the absorbent body 4, and to prevent the body fluid absorbed in the absorbent body 4 from leaking from end portions.

FIG. 4-(A) is a plan view illustrating only the absorbent body emboss 23 provided from the front surface of the absorbent body 4. As illustrated in FIG. 4-(A), the absorbent body emboss 23 is configured to include linear absorbent body embosses 26, provided at both sides of the body fluid expelling portion H in the width direction, respectively, as straight lines extending along the pad-longitudinal direction.

By providing the linear absorbent body embosses 26, the body fluid absorbed in the absorbent body 4 and diffusing in the width direction is blocked and the body fluid is prevented from leaking from the side edges of the absorbent body 4.

In this description, "extend along the longitudinal direction of the incontinence pad 1" means that a straight line connecting end portions of the emboss substantially extends along the longitudinal direction of the incontinence pad 1, and includes, in addition to a case in which the straight line is parallel to a longitudinal direction line, a case in which the straight line has an angle difference with respect to the longitudinal direction line within about ±40°. Further, similarly, "extend along the width direction of the incontinence pad 1" means that a straight line connecting end portions of the emboss substantially extends along the width direction of the incontinence pad 1, and includes, in addition to a case in which the straight line is parallel to a width direction line, a case in which the straight line has an angle difference with respect to the width direction line within about ±40°. Further, the emboss line that extends along the longitudinal direction or the width direction is unnecessarily a straight line, and may be formed by a curved line, a polygonal line, a wavy line or the like.

The linear absorbent body emboss 26 is a single linear emboss or a plurality of linear embosses with a space therebetween in the pad-width direction, each provided as a continuous line or an intermittent line extending along the pad-longitudinal direction at each of both sides of the body fluid expelling portion H in the width direction, and is configured by a straight line, a curved line, a wavy line or the like. For the example illustrated in FIG. 1, the linear absorbent body emboss 26 is formed by a single continuous straight line extending along the pad-longitudinal direction at each of the both sides of the body fluid expelling portion H. The linear absorbent body emboss 26 is provided not to overlap the front surface emboss 24. The linear absorbent body emboss 26 may be formed as a plane pattern in a predetermined area like a mesh shape such as a lattice-shape, a rhombic lattice-shape, a honeycomb-shape or the like.

The linear absorbent body emboss 26 is formed to include a range that overlaps the body fluid expelling portion H in the pad-width direction. Preferably, as illustrated in FIG. 1, the linear absorbent body emboss 26 is formed at a range equal to the standing gathers BS at both sides in the pad-longitudinal direction, or at a range that extends outside of the standing gathers BS at both sides in the pad-longitudinal direction. With this, even when the body fluid absorbed in the area corresponding to the body fluid expelling portion H diffuses in the pad-width direction, leakage of the body fluid from side portions of the absorbent body 4 in the lateral direction can be surely prevented and the body fluid blocked by the standing gathers BS can be surely absorbed and retained in the absorbent body 4.

It is preferable that the linear absorbent body emboss 26 is provided in the vicinity of a side edge of the absorbent body 4, concretely, at an inner position of the side edge of the absorbent body 4 by 3 mm to 10 mm. With this, the body fluid can diffuse in a broader range of the absorbent body 4, and the maximum absorbing volume of the absorbent body 4 can be used. As illustrated in FIG. 1, it is preferable that all of or a part of the linear absorbent body emboss 26 is provided at a position that overlaps the side non-woven fabric 7 that constitutes the standing gather BS in a thickness direction. With this, the body fluid blocked by the standing gather BS can be surely absorbed and retained in the absorbent body 4. Here, the linear absorbent body emboss 26 may be provided inside of the side non-woven fabric 7.

Meanwhile, the front surface emboss 24 is an emboss that is provided, after stacking the liquid permeable topsheet 3 on the front surface (skin surface) of the absorbent body 4, by integrally compressing from the front surface of the liquid permeable topsheet 3 (skin surface) to the absorbent body 4. Similar to the absorbent body emboss 23, the front surface emboss 24 is provided to block and prevent the body fluid that diffuses in the absorbent body 4 from leaking from the end portions of the absorbent body 4, and to block the body fluid that flows along a groove of a body such as a groove of the body fluid expelling portion, a groove of a hip portion or the like to be flowed into the emboss and to be absorbed and retained in the absorbent body 4.

FIG. 4-(B) is a plan view illustrating only the front surface emboss 24 that is provided from the front surface of the liquid permeable topsheet 3. As illustrated in FIG. 4-(B), the front surface emboss 24 may be formed by curved lines such as arc lines, elliptical lines or the like, provided at front and rear portions of the area corresponding to the body fluid expelling portion H in the longitudinal direction, respectively, each extending along the pad-width direction while bulging outwardly in the pad-longitudinal direction. The reason why the body fluid flows at the front surface of the liquid permeable topsheet 3 is often due to the fact that the body fluid flows along the groove of the body such as the groove of the body fluid expelling portion, the groove of the hip portion or the like. Thus, in order to effectively trap this flowed body fluid, it is preferable to provide the front surface emboss 24 at each of front and rear portions of the area corresponding to the body fluid expelling portion H in the longitudinal direction. Further, by forming the front surface emboss 24 by the curved line that extends along the pad-width direction while bulging outwardly in the pad-longitudinal direction, the body fluid flowing in the front and rear directions at the center portion in the width direction can be surely flowed in the emboss grooves. Here, the front surface emboss 24 may be formed by a straight line, a wavy line or the like that extends along the pad-width direction.

It is preferable that the front surface emboss 24 is provided at each of front and rear portions of the body fluid expelling portion H in the longitudinal direction, respectively, as a single emboss extending along the pad-width direction, or a plurality of embosses, each extending along the pad-width direction, with a space therebetween in the pad-longitudinal direction. For the example illustrated in FIG. 4-(B), the single front surface emboss 24 is provided at a front side of the body fluid expelling portion H, and two of the front surface embosses 24 are provided at a rear side of the body fluid expelling portion H with a space in the pad-longitudinal direction. As the body fluid tends to flow at the rear side of the body fluid expelling portion H along the groove of the hip portion, it is preferable to provide the plurality of the front surface embosses 24 to effectively block the body fluid.

The absorbent body embosses 23 and the front surface embosses 24 are provided at positions not to overlap with each other. This means that when providing the front surface emboss 24 from the front surface of the liquid permeable topsheet 3, the front surface emboss 24 is formed by integrally compressing constituent members from the liquid permeable topsheet 3 to the absorbent body 4, to the absorbent body 4 at which the emboss is not yet formed. The absorbent body emboss 23 and the front surface emboss 24 do not overlap with each other means that all of or a part of the front surface emboss 24 does not overlap all of or a part of the absorbent body emboss 23.

Figure 5:
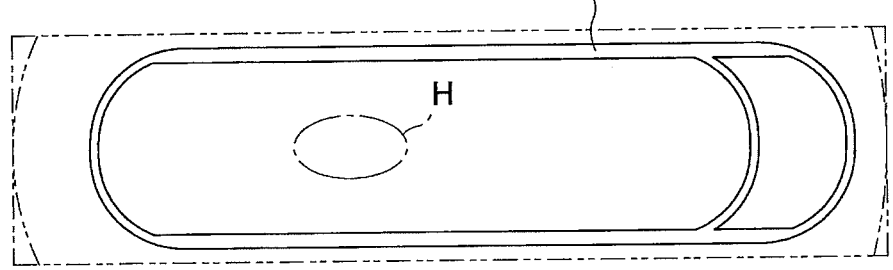
FIG. 5-(A) is a plan view of an emboss provided to an absorbent body of a conventional absorbent article, FIG. 5-(B) is a plan view of an emboss provided at a front surface and FIG. 5-(C) is a plan view in which these are overlapped.
Figure 5:
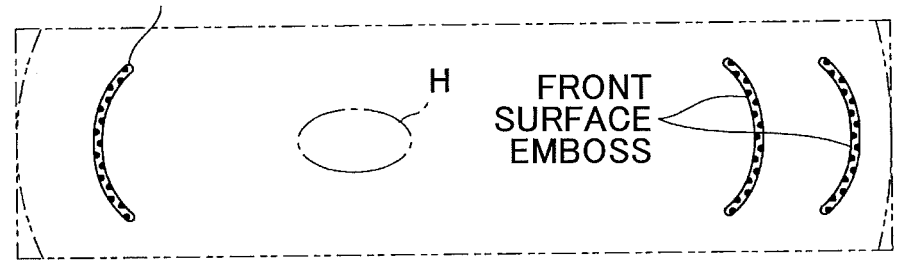
Figure 5:
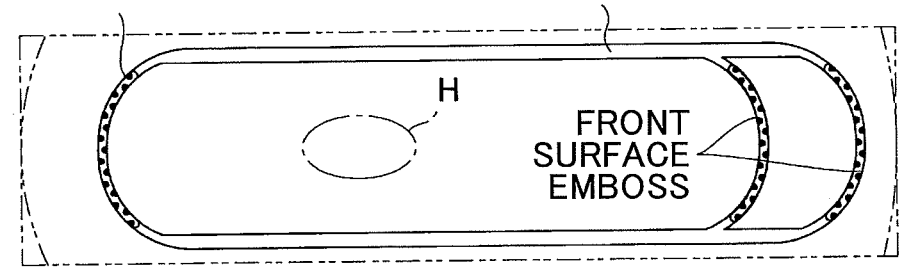

Effects of the incontinence pad 1 with the above described configuration are described. For the conventional absorbent article as illustrated in FIG. 5-(A), a closed emboss line that surrounds the body fluid expelling portion H is formed by compression from a front surface of the absorbent body or a front surface of the liquid permeable topsheet at once. In such a case, a difference in a compression direction or a compressed degree occurs at a boundary portion between a feed direction of a manufacturing line (MD direction) and a perpendicular direction (CD direction) when embossing. Thus, there are problems such as wrinkles, twists, deformations or the like are generated so that the emboss is not properly formed because distortion of compressive force applied to a front sheet tends to be accumulated, and runnability is worsened because the number of dispersion sites of pressure is small and a product twists around an emboss roller as emboss portions bite emboss protruding portions of the emboss roller. On the other hand, according to the incontinence pad 1, as illustrated in FIG. 4, as the closed emboss line that surrounds the body fluid expelling portion H is constituted by the absorbent body emboss 23 and the front surface emboss 24, and these absorbent body emboss 23 and the front surface emboss 24 are separately provided, force applied to materials is dispersed, wrinkles, twists or the like are reduced and the embosses are fairly processed. Further, as the pressure when performing the emboss compression is dispersed between the absorbent body emboss 23 and the front surface emboss 24, twisting around the emboss roller does not occur and runnability becomes stable.

Further, as illustrated in FIG. 5, according to the conventional absorbent article, there is a risk that a user feels hardness of a product and feels uncomfortable when wearing the product if the front surface emboss is provided to overlap the absorbent body emboss. On the other hand, according to the incontinence pad 1, as the front surface emboss 24 is provided not to overlap the absorbent body emboss 23, compared with a case that the front surface emboss 24 is provided to overlap the absorbent body emboss 23, the phenomenon that the emboss becomes stiff to worsen the fittability can be prevented.

Here, it is preferable that the absorbent body emboss 23 and the front surface emboss 24 are provided to be connected with each other or provided in the vicinity with each other. It is preferable that the absorbent body emboss 23 and the front surface emboss 24 are connected with each other from a view point that the diffusion of the body fluid toward outside is suppressed. However, when providing the side non-woven fabrics 7 for forming the standing gathers BS at both side portions at the skin surface side, as the incontinence pad 1, the front surface emboss 24 may be apart from the absorbent body emboss 23 such that not to overlap the respective side non-woven fabric 7. When the absorbent body emboss 23 and the front surface emboss 24 are apart from each other, the distance width in the pad-width direction may be less than or equal to 15 mm, preferably, less than or equal to 5 mm.

Figure 6:
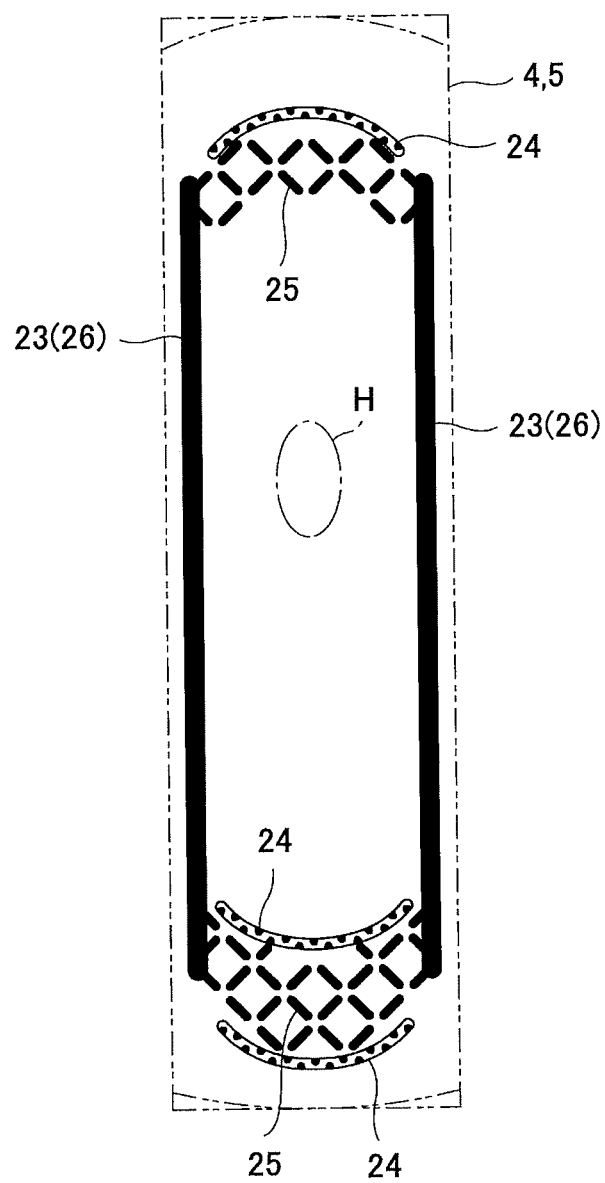
FIG. 6 is a plan view for a case in which a lattice-shaped absorbent body emboss 25 is provided.

As illustrated in FIG. 6, the absorbent body emboss 23 may include lattice-shaped absorbent body embosses 25, provided at front and rear portions of the area corresponding to the body fluid expelling portion H in the longitudinal direction, respectively, each formed at an area extending along the width direction of the incontinence pad 1. The lattice-shaped absorbent body embosses 25 are provided in manufacturing steps with the linear absorbent body embosses 26 from the front surface of the absorbent body 4 or the encapsulating sheet 5. Similar to the linear absorbent body embosses 26, the lattice-shaped absorbent body embosses 25 are provided not to overlap the front surface emboss 24.

Similar to the linear absorbent body emboss 26, the lattice-shaped absorbent body emboss 25 may be formed by a straight line, a curved line, a wavy line or the like, and it is preferable to be formed such that its plane shape is a lattice-shape in which emboss is placed intermittently at each intersection, and is a rhombic lattice-shape in which strips of the lattice are inclined for about 45° with respect to the longitudinal direction and the width direction of the napkin. When the line transferring direction of the product matches the pad-longitudinal direction in manufacturing steps, if the lattice-shaped absorbent body emboss 25 is formed in a square lattice-shape in which strips of the lattice substantially match the longitudinal direction and the width direction of the napkin, a difference becomes large between an area at which linear pressure in compression by an emboss roller becomes high and an area at which the linear pressure becomes low. Thus, splits, wrinkles, twists or the like of the front surface material by compression are easily generated. On the other hand, if the lattice-shaped absorbent body emboss 25 is formed in a rhombic lattice-shape, as the linear pressure becomes substantially uniform, splits or the like of the front surface material can be prevented. Further, by providing the lattice-shaped absorbent body emboss 25 in a rhombic lattice-shape, the body fluid diffusing in front and rear directions from a center portion can be received by both strips of the lattice perpendicular to each other, and diffusion of the body fluid toward outside can be effectively suppressed. Further, by forming the emboss intermittently at each intersection, twisting around the emboss roller or blocking of paper powders in the emboss roller can be prevented in compression of the emboss. Here, it is preferable that a providing area of the lattice-shaped absorbent body emboss 25 is a curved area that bulges outwardly in the pad-longitudinal direction in accordance with the curved line shape of the front surface emboss 24.

It is preferable that the lattice-shaped absorbent body emboss 25 is provided such that both end portions thereof are connected to the linear absorbent body embosses 26 or in the vicinity of the linear absorbent body embosses 26, respectively. It is more preferable that the lattice-shaped absorbent body emboss 25 is provided to be connected to the linear absorbent body embosses 26 in order to suppress the body fluid from diffusing outward from spaces between the linear absorbent body embosses 26 and the lattice-shaped absorbent body emboss 25.

The lattice-shaped absorbent body emboss 25 may be formed with a groove width same as or larger than that of the linear absorbent body emboss 26, but it is preferable that the lattice-shaped absorbent body emboss 25 is formed with a groove width smaller than that of the linear absorbent body emboss 26. This means that the linear absorbent body emboss 26 may be formed with a groove width larger than that of the lattice-shaped absorbent body emboss 25. As described above, as it is preferable for the lattice-shaped absorbent body emboss 25 to be formed in a mesh shape, if the lattice-shaped absorbent body emboss 25 is formed with a border width, there is a risk that fittability is worsened because hardness of the absorbent body 4 increases. Here, as the front surface emboss 24 is formed at each of the front and rear portions of the body fluid expelling portion H in the longitudinal direction, the blocking effect of the body fluid can be maintained even when the lattice-shaped absorbent body emboss 25 is formed with a narrow groove width, by a synergy effect with the front surface emboss 24.

By connecting the lattice-shaped absorbent body emboss 25 to the linear absorbent body emboss 26, even when the absorbent body emboss 23 and the front surface emboss 24 are apart from each other, the body fluid is prevented from diffusing outward from the divided portion.

It is preferable that the front surface emboss 24 is provided at least outward of the lattice-shaped absorbent body emboss 25. With this, diffusion of the body fluid in the absorbent body 4 and diffusion of the body fluid that flows at the front surface can be surely suppressed. For the example illustrated in FIG. 6, the front surface emboss 24 is provided only at an outer side for the front side lattice-shaped absorbent body emboss 25 and the front surface embosses 24 are provided at an outer side and at an inner side, respectively, for the rear side lattice-shaped absorbent body emboss 25. It is preferable that a plurality of the front surface embosses 24 are provided as the flow of the body fluid that flows along the groove of the hip portion easily occurs at the rear side of the body fluid expelling portion H.

Alternative Example

Figure 7:
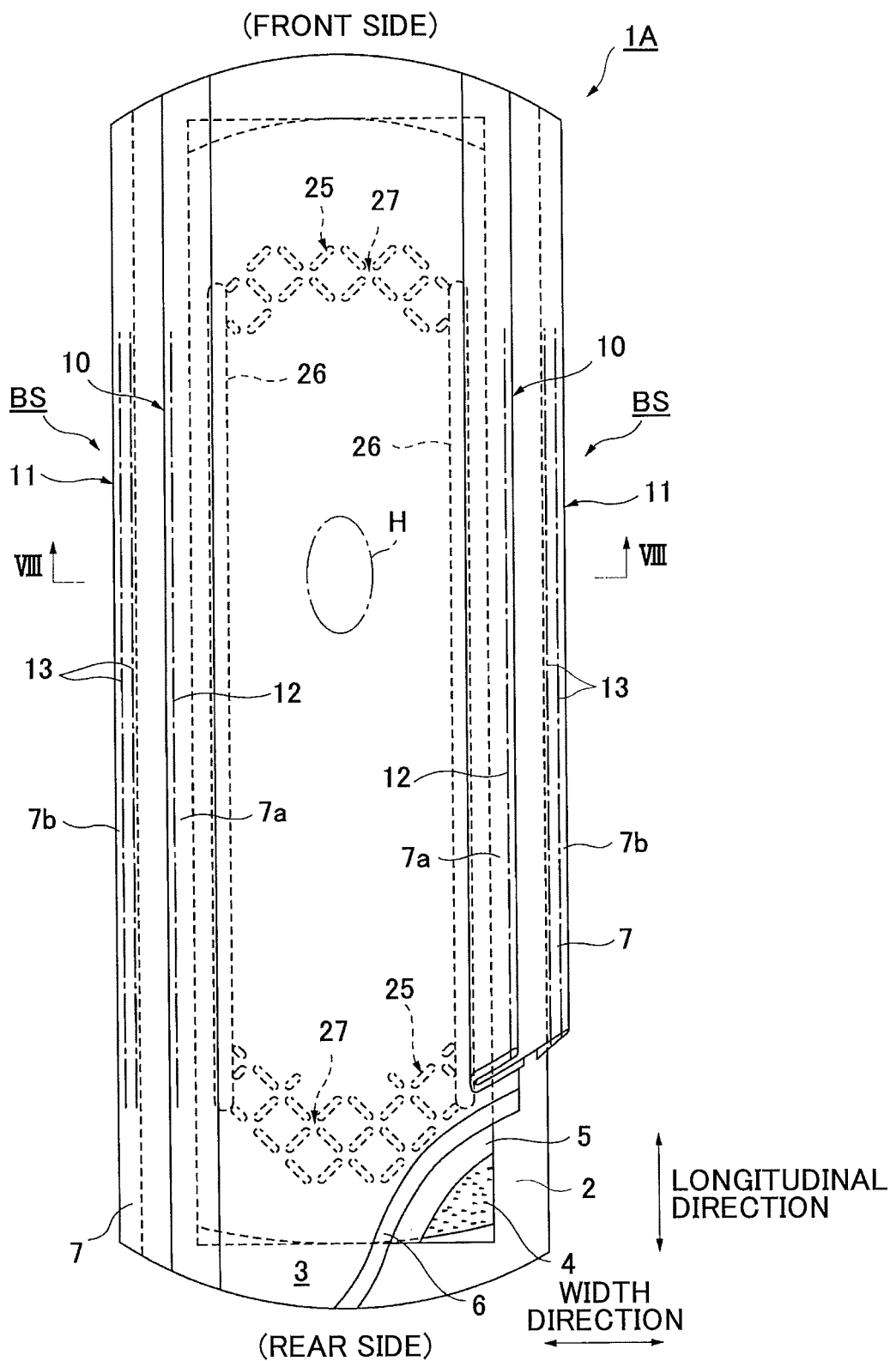
FIG. 7 is a partially broken developed view of an incontinence pad 1A of an alternative example.
Figure 8:
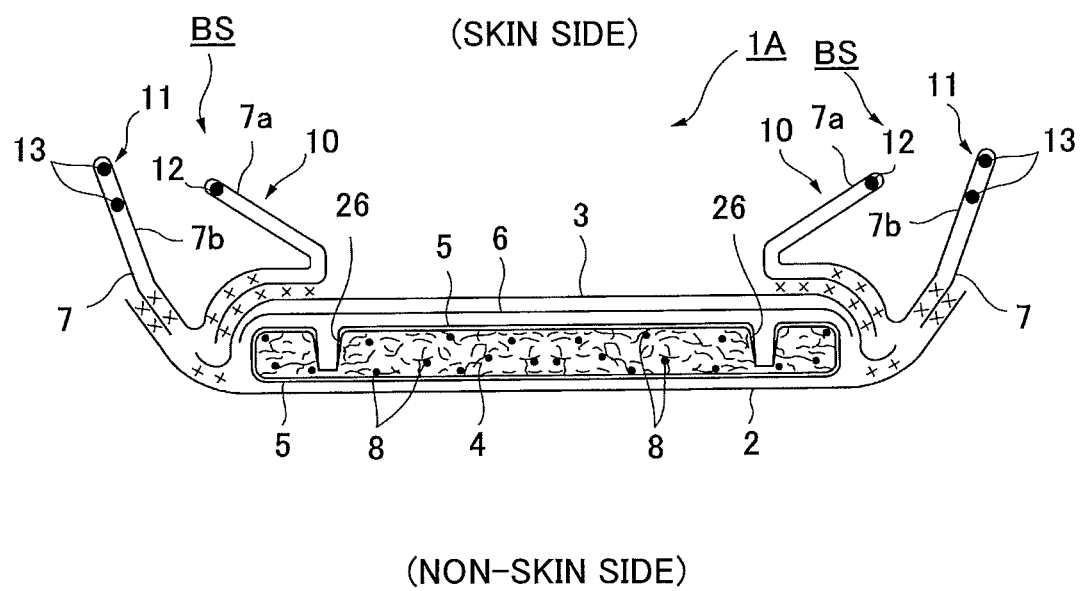
FIG. 8 is a cross-sectional view taken along a VIII-VIII line of FIG. 7 (a lateral cross-sectional view of the incontinence pad 1A)

As illustrated in FIG. 7, the lattice-shaped absorbent body emboss 25 having a lattice-shape in a plane view is provided at a predetermined area in an incontinence pad 1A of an alternative example. Here, the front surface emboss 24 may not be provided as illustrated in FIG. 7, or may be provided similarly as the example illustrated in FIG. 6 in the incontinence pad 1A of the alternative example. The lattice-shaped absorbent body emboss 25 is provided with the intermittent portions 27, by which the emboss groove is placed intermittently, at crossing portions of the strips of the lattice, respectively. Further, the lattice-shaped absorbent body emboss 25 is provided as a rhombic lattice in which the direction of the strips of the lattice is inclined with respect to the longitudinal direction and the width direction of the incontinence pad 1A.

It is preferable that the lattice-shaped absorbent body emboss 25 is provided at each of front and rear areas of the area corresponding to the body fluid expelling portion H, respectively, within an area extending along the pad-width direction. Further, the linear absorbent body embosses 26, which are straight lines extending along the pad-longitudinal direction, are provided at both sides of the area corresponding to the body fluid expelling portion H in the width direction. It is preferable to provide the lattice-shaped absorbent body embosses 25 and the linear absorbent body embosses 26 to surround the area corresponding to the body fluid expelling portion H.

In this description, an area extending along the width direction of the incontinence pad 1A means that a straight line connecting end portions of the emboss area is substantially extending along the width direction of the incontinence pad 1A, and includes, in addition to a case in which the straight line is parallel to a width direction line, a case in which the straight line has an angle difference with respect to the width direction line within about ±40°. Further, similarly, an area extending along the longitudinal direction of the incontinence pad 1A means that a straight line connecting end portions of the emboss area is substantially extending along the longitudinal direction of the incontinence pad 1A, and includes, in addition to a case in which the straight line is parallel to a longitudinal direction line, a case in which the straight line has an angle difference with respect to the longitudinal direction line within about ±40°. Further, the area extending along the longitudinal direction or the width direction is not necessarily a straight line, and may be formed by a curved line, a polygonal line, a wavy line or the like.

Figure 9:
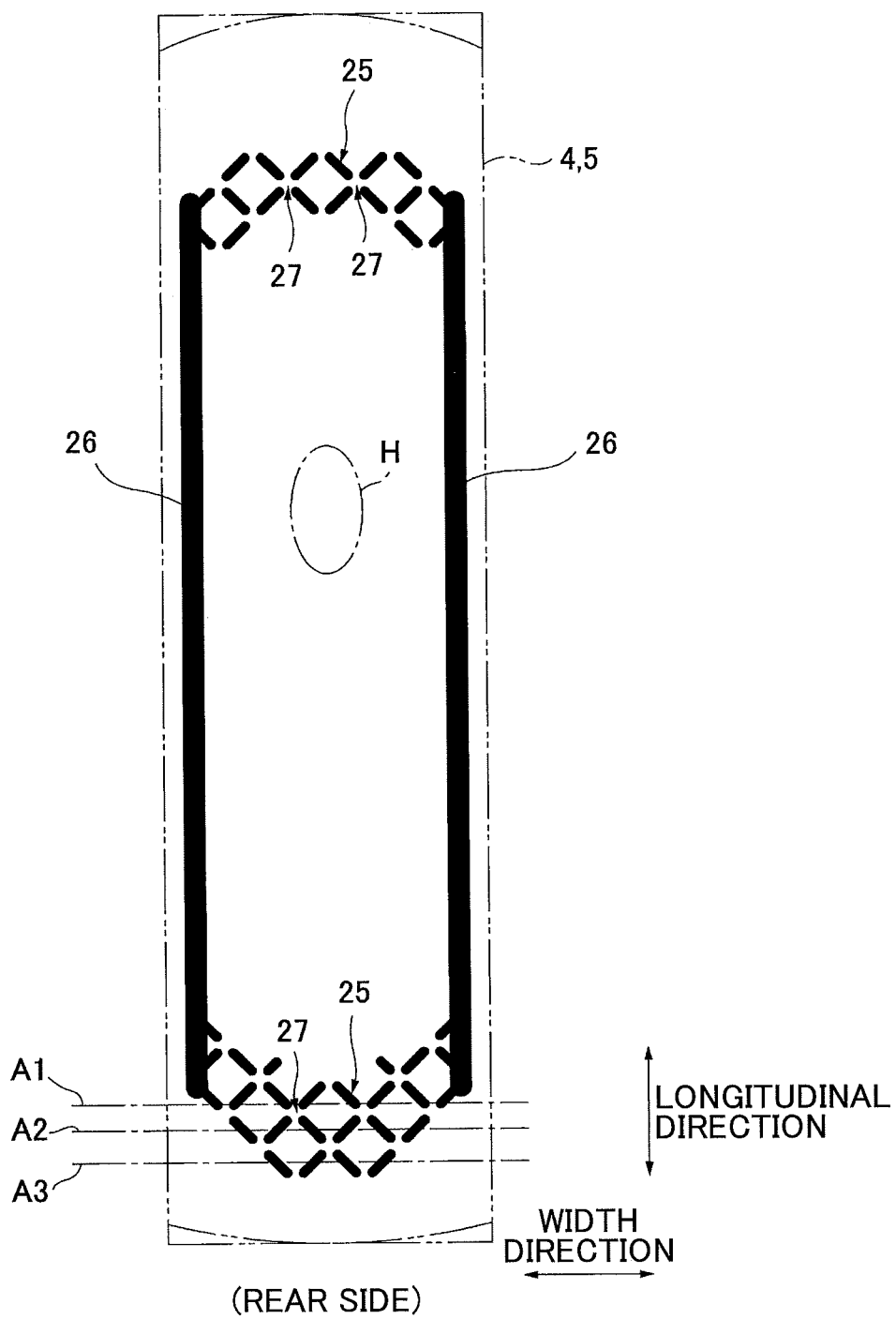
FIG. 9 is a plan view of an absorbent body emboss.

It is preferable that the lattice-shaped absorbent body emboss 25 and the linear absorbent body emboss 26 are provided from the front surface (skin surface side) of the absorbent body 4 or the encapsulating sheet 5 that encapsulates the absorbent body 4 before stacking the liquid permeable topsheet 3. This means that, as illustrated in FIG. 9, the lattice-shaped absorbent body emboss 25 and the linear absorbent body emboss 26 are provided by compression from the front surface of the absorbent body 4 or the encapsulating sheet 5 in the manufacturing steps of the incontinence pad 1A. The lattice-shaped absorbent body emboss 25 and the linear absorbent body emboss 26 block the body fluid absorbed in the absorbent body 4 from diffusing in the absorbent body 4 to prevent the body fluid from leaking from end portions of the absorbent body 4.

By providing the lattice-shaped absorbent body emboss 25 and the linear absorbent body emboss 26, the body fluid absorbed in the absorbent body 4 is surely blocked by the lattice-shaped absorbent body emboss 25 and the linear absorbent body emboss 26 so that the leakage of the body fluid from the end portions of the absorbent body 4 can be completely prevented. Here, the linear absorbent body emboss 26 may not be provided, but it is preferable to provide the linear absorbent body emboss 26 as well in order to surely prevent the leakage from end portions in the width direction of the absorbent body 4.

Figure 10:
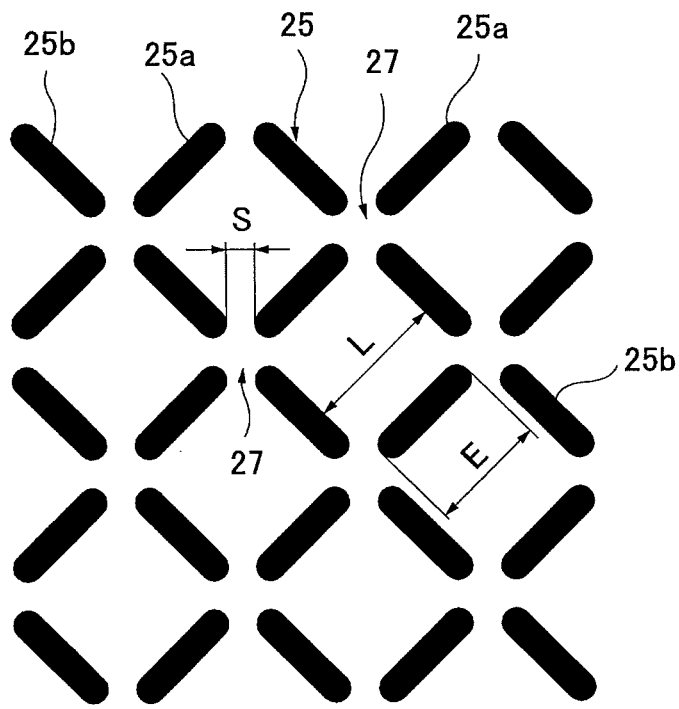
FIG. 10 is an enlarged plan view of the lattice-shaped absorbent body emboss 25.

As illustrated in FIG. 10 in detail, the lattice-shaped absorbent body emboss 25 is formed in a lattice-shaped shape constituted by a plurality of first emboss grooves 25a extending in a first direction and a plurality of second emboss grooves 25b extending in a second direction that is perpendicular to the first direction. Further, the intermittent portions 27 are formed at intersections of the first emboss grooves 25a and the second emboss grooves 25b at which the emboss grooves 25a and 25b are placed intermittently. Further, each of the first direction and the second direction is inclined with respect to the longitudinal direction and the width direction of the incontinence pad 1A with an angle of about 45°. By providing the intermittent portions 27, the lattice-shaped absorbent body emboss 25 is formed as intermittent lines in which the first emboss grooves 25a and the intermittent portions 27 are alternatively provided in the first direction, and as intermittent lines in which the second emboss grooves 25b and the intermittent portions 27 are alternatively provided in the second direction.

The length (space) of the intermittent portion 27 may be 2 mm to 5 mm, and preferably, may be 2 mm to 3 mm. The length of the intermittent portion 27 means the maximum space S between the adjacent emboss grooves. By setting the length of the intermittent portion 27 to such a range, the pressure can be appropriately divided when performing embossing, and the body fluid can be appropriately dispersed outward without reducing the blocking effect of the body fluid.

As illustrated in FIG. 10, it is preferable that the length L (the distance width between the adjacent emboss grooves that are inclined in the same direction) of one side of the lattice formed by the lattice-shaped absorbent body emboss 25 is about 8 mm to 15 mm. Further, it is preferable that the length E of the emboss groove provided at each of the sides of the lattice is about 5 mm to 12 mm. If the square of the lattice is too small, runnability becomes bad, while if the square of the lattice is too large, a user may tend to feel hardness of the emboss grooves when being worn, and it is not preferable.

The size of the lattice-shaped absorbent body emboss 25 may be the same or different at a front side portion and a rear side portion of the area corresponding to the body fluid expelling portion H. For example, as the body fluid tends to be reserved at the rear side portion by flowing along the skin surface, in order to improve the outward diffusibility, the length of the intermittent portion 27 may be made longer.

As illustrated in FIG. 9, it is preferable that the providing area of the lattice-shaped absorbent body emboss 25 is a curved shape in which outlines at both ends in the longitudinal direction bulge outwardly in the pad-longitudinal direction. With this, the body fluid that spokewisely diffuses from the area corresponding to the body fluid expelling portion H at the pad center portion can be surely blocked.

Further, as illustrated in FIG. 9, it is preferable that the providing area of the lattice-shaped absorbent body emboss 25 is formed such that its width becomes narrower toward the end portion in the longitudinal direction of the absorbent body 4 at least at the rear side of the body fluid expelling portion H. With this, the number of compressed portions decrease toward the rear side (end portion side), such as the numbers of the compressed portions on width direction lines expressed by A1 to A3 become eight at A1, six at A2 and four at A3. Thus, hardness at the end portion side by the compression is lowered and uncomfortable feeling when being worn can be reduced. Further, by similarly forming the providing area of the lattice-shaped absorbent body emboss 25 at the front side of the body fluid expelling portion H such that its width becomes narrower toward the end portion in the longitudinal direction, uncomfortable feeling when being worn can be reduced.

Meanwhile, the linear absorbent body emboss 26 is provided as a continuous line or an intermittent line extending along the pad-longitudinal direction at each of both sides of the area corresponding to the body fluid expelling portion H in the width direction. The linear absorbent body emboss 26 is a single emboss or a plurality of linear embosses, with a space in the pad-width direction. The linear absorbent body emboss 26 is constituted by a straight line, a curved line, a wavy line or the like. For the example illustrated in FIG. 9, the linear absorbent body emboss 26 is formed by a straight continuous line extending along the pad-longitudinal direction at each of both sides of the area corresponding to the body fluid expelling portion H. The linear absorbent body emboss 26 may be provided from the front surface of the absorbent body 4 or the encapsulating sheet 5 with the lattice-shaped absorbent body emboss 25 or may be provided separately from the lattice-shaped absorbent body emboss 25, in manufacturing steps. The linear absorbent body emboss 26 may be formed in a mesh shape such as a lattice-shape, a rhombic lattice-shape, a honeycomb-shape or the like.

The linear absorbent body emboss 26 is formed to include at least a range that overlaps the area corresponding to the body fluid expelling portion H in the pad-width direction. As illustrated in FIG. 9, it is preferable that the linear absorbent body emboss 26 is provided such that both end portions thereof extend to positions connected to or in the vicinity of both side portions of the lattice-shaped absorbent body embosses 25 provided at front and rear portions of the area corresponding to the body fluid expelling portion H. With this, when the body fluid absorbed in the absorbent body 4 diffuses in the pad-width direction, leakage in the lateral direction from side portions of the absorbent body 4 can be surely prevented.

Figure 11:
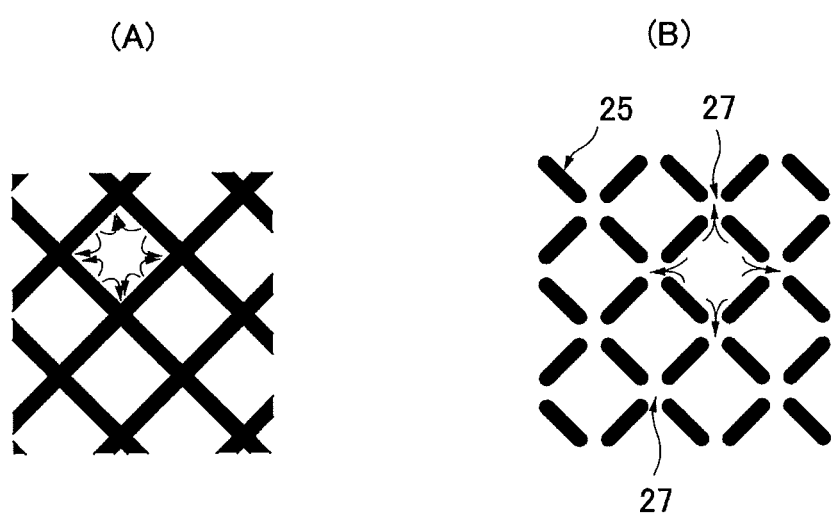
FIG. 11-(A) is an enlarged plan view of a conventional lattice-shaped emboss, and FIG. 11-(B) is an enlarged plan view of the lattice-shaped absorbent body emboss 25 of the invention.

By providing the lattice-shaped absorbent body emboss 25 formed as such, next effects can be obtained in the incontinence pad 1A. As illustrated in FIG. 11-(A), for the case of the conventional lattice-shaped emboss, in which the intermittent portions 27 are not formed and each of the squares of the lattice is surrounded by the continuous emboss groove, as pressure applied to a front surface material (front surface of the encapsulating sheet 5 or the absorbent body 4) in emboss compression cannot be dispersed, distortion by the compression is accumulated, and wrinkles, twists or the like are easily generated in the front surface material. By the generation of the wrinkles or the twists, there is a problem of runnability because a product twists around the emboss roller as emboss grooves bite the emboss protruding portions of the emboss roller. On the other hand, for the incontinence pad 1A, as illustrated in FIG. 11-(B), as the pressure applied to the front surface material in emboss compression is dispersed by the intermittent portions 27, and there are escapeways of the distortion applied to the front surface material, wrinkles, twists or the like of the front surface material are not easily generated. Thus, twisting of the product around the emboss roller can be prevented. Further, as the crossing portions are not formed in the emboss groove, a problem such as paper powders are blocked at the corner portions of the crossing portions can be solved and runnability of the emboss process can be improved.

Further, as illustrated in in FIG. 12-(A), when the line transferring direction of the product in the manufacturing steps matches the pad-longitudinal direction, and if the lattice-shaped absorbent body emboss is formed in a square lattice-shape in which strips of the lattice extend substantially the same as the pad-longitudinal direction and the width direction, the emboss groove is formed in directions that match the pad-longitudinal direction and the width direction. Thus, a difference becomes large between a portion at which the linear pressure is high and a portion at which the liner pressure is low in compression by the emboss roller, and splits, wrinkles, twists or the like of the front surface material by the compression are easily generated. On the other hand, as illustrated in FIG. 12-(B), when the lattice-shaped absorbent body emboss is placed in a rhombic lattice-shape as the incontinence pad 1A, as the emboss groove is provided substantially uniform with respect to the pad-width direction, the linear pressure becomes substantially uniform and splits or the like of the front surface material can be prevented.

Further, by providing the lattice-shaped absorbent body emboss in a rhombic lattice-shape, the body fluid diffused from the center portion toward the front and rear directions can be blocked by both strips of the lattice perpendicular to each other and the diffusion of the body fluid toward outside can be effectively suppressed.

Regarding effects of the lattice-shaped absorbent body emboss 25, FIG. 13 to FIG. 15 illustrate comparison between conventionally known lattice-shaped embosses, line-shaped embosses, and a dot-shaped emboss. As illustrated in FIG. 13, for examples 1 and 2, in which the lattice-shaped absorbent body emboss 25 is adopted, "blockings of a pattern" and "splits" do not occur, "runnability" is good, "compressed degree" is good, "diffusion prevention ability" for the body fluid is good, and "hardness" is not felt when being worn. The sample in which the length of the intermittent portion 27 is 2 mm is particularly good in the "diffusion prevention ability" for the body fluid.

Further, for comparative example 1, in which a rhombic lattice-shaped emboss is formed by crossing emboss grooves, as there are no escapeways for pressure in emboss compression, twisting round the emboss roller, blockings of paper powders and the like occur, and "runnability" is worsened.

For comparative example 2, the emboss grooves are continuously formed at crossing portions, similar to comparative example 1, but are apart from each other at middle portions. Similar to comparative example 1, as there are crossing portions of the emboss grooves in comparative example 2, blockings of the emboss roller and the like occur, and "runnability" is worsened. Further, a difference in "compressed degree" occurs and uniform compression cannot be performed.

For comparative example 3, intermittent portions are provided at crossing portions, respectively, similar to examples 1 and 2, but the emboss is provided in a square lattice-shape in which strips of the lattice match the pad-longitudinal direction and the width direction. Thus, as described above, a difference in "compressed degree 2 occurs and "runnability" is worsened.

As illustrated in FIG. 15, for comparative examples 4 and 5, a plurality of line-shaped embosses that extend along the pad-longitudinal direction and apart from each other in the pad-width direction are provided. In such a case, although sufficient "runnability" and absorbent ability can be obtained, there was a problem that a user feels hardness of the emboss groove when wearing the sample, and texture and fit feeling are worsened. Here, although a line width of the line-shaped emboss is different in comparative example 4 and comparative example 5, there were no difference in performances by this difference.

Further, for comparative example 6, dot-shaped embosses are provided in a staggered manner. However, as these are the dot-shaped embosses, "compressed degree" is weak and absorbent ability was not good compared with other samples.

Other Embodiments (1) In the above described embodiment, a lattice-shaped emboss, which has a lattice-shape in a plane view, is provided as the lattice-shaped absorbent body emboss 25 that is included in a concept of the absorbent body emboss 23, formed from the front surface of the absorbent body 4 or the encapsulating sheet 5 that encapsulates the absorbent body 4 before stacking the liquid permeable topsheet 3. The lattice-shaped emboss may be provided as a lattice-shaped front surface emboss included in a concept of the front surface emboss 24 formed from the front surface of the liquid permeable topsheet 3 after stacking the liquid permeable topsheet 3 at a skin side of the absorbent body 4.

(2) Instead of the linear absorbent body embosses 26, the lattice-shaped absorbent body embosses 25 or lattice-shaped embosses configured similarly as the lattice-shaped front surface embosses may be provided at areas extend along the pad-longitudinal direction at both sides of the area corresponding to the body fluid expelling portion H in the pad-width direction.

(3) In the incontinence pad 1 or 1A, a concave groove for the body fluid to be flowed therein may be formed at a front surface of the area corresponding to the body fluid expelling portion H along the longitudinal direction. The concave groove is for receiving the body fluid ejected at the front surface of the liquid permeable topsheet 3, temporarily reserving the body fluid, inducing the diffusing of the body fluid in front and rear directions, increasing the absorbing speed of the body fluid in the absorbent body 4, and preventing the leakage in the lateral direction.

The concave groove may be provided by previously forming an absorbent body concave portion of a concave groove or a slit in the absorbent body 4 along the longitudinal direction at a skin contacting surface including the body fluid expelling portion H, not by compression, encapsulating the absorbent body 4 by the encapsulating sheet 5, stacking the liquid permeable topsheet 3, and then, in accordance with necessity, forming an emboss portion in the absorbent body concave portion along the absorbent body concave portion by embossing from the front surface of the liquid permeable topsheet 3 (skin contacting surface). In addition to this, the concave groove may be provided, after stacking the liquid permeable topsheet 3 on the absorbent body 4, by compression from the front surface of the liquid permeable topsheet 3 by integrally compressing constituent members from the liquid permeable topsheet 3 to the absorbent body 4.

The concave groove may be formed as single concave groove at a center portion in the pad-width direction corresponding to the body fluid expelling portion H at a middle portion in the longitudinal direction, as a plurality of concave grooves provided with a space therebetween in the pad-width direction, or as a discontinuous line formed to be apart from each other in the pad-longitudinal direction.

NUMERALS

1 . . . incontinence pad, 2 . . . liquid impermeable backsheet, 3 . . . liquid permeable topsheet, 4 . . . absorbent body, 5 . . . encapsulating sheet, 6 . . . second sheet, 7 . . . side non-woven fabric, 8 . . . superabsorbent polymer, 10 . . . inner standing gather, 11 . . . outer standing gather, 12, 13 . . . threadlike elastic stretchable member, 23 . . . absorbent body emboss, 24 . . . front surface emboss, 25 . . . lattice-shaped absorbent body emboss, 26 . . . linear absorbent body emboss, 27 . . . intermittent portion

What is claimed is:

1. An absorbent article in which an absorbent body is provided between a liquid permeable topsheet and a backsheet, comprising:
    an absorbent body compressed part provided from a front surface side of the absorbent body before stacking the liquid permeable topsheet to surround an area corresponding to a body fluid expelling portion; and
    a front surface compressed part, formed separately from the absorbent body compressed part and not to overlap the absorbent body compressed part, provided from a front surface side of the liquid permeable topsheet,
    wherein the absorbent body compressed part is provided so as to overlap a portion of the liquid permeable topsheet that has no compressed part.

2. The absorbent article according to claim 1,
    wherein the absorbent body compressed part includes linear absorbent body compressed parts, provided at both sides of the area corresponding to the body fluid expelling portion in a width direction, respectively, each extending along a longitudinal direction of the absorbent article, and
    wherein the front surface compressed part is formed by curved lines, provided at front and rear portions of the area corresponding to the body fluid expelling portion in the longitudinal direction, respectively, each extending along the width direction of the absorbent article while bulging outwardly in the longitudinal direction.

3. The absorbent article according to claim 1, wherein the absorbent body compressed part and the front surface compressed part are connected with each other, or provided in the vicinity with each other.

4. The absorbent article according to claim 1, wherein the front surface compressed part is provided at each of front and rear portions of the area corresponding to the body fluid expelling portion in the longitudinal direction, respectively, as a single compressed part extending along the width direction, or a plurality of compressed parts, each extending along the width direction, with a space therebetween in the longitudinal direction.

5. The absorbent article according to claim 1, wherein the absorbent body compressed part includes lattice-shaped absorbent body compressed parts, provided at front and rear portions of the area corresponding to the body fluid expelling portion in the longitudinal direction, respectively, each formed at an area extending along the width direction of the absorbent article.

6. The absorbent article according to claim 5, wherein each of the lattice-shaped absorbent body compressed parts is provided with intermittent portions at which compressed grooves are placed intermittently at crossing portions of strips of the respective lattice-shaped absorbent body, and is formed in a rhombic lattice-shape in which strips of the respective lattice-shaped absorbent body is inclined with respect to the longitudinal direction and the width direction of the absorbent article.

7. The absorbent article according to claim 6,
wherein the length of each of the intermittent portions is 2 to 5 mm.

8. The absorbent article according to claim 5,
wherein a concave groove is provided at a skin contacting surface at the area corresponding to the body fluid expelling portion along the longitudinal direction, and
wherein the lattice-shaped absorbent body compressed parts are provided at front and rear areas of the concave groove, respectively.

9. The absorbent article according to claim 1, wherein the front surface compressed part includes lattice-shaped front surface compressed parts, provided at front and rear portions of the area corresponding to the body fluid expelling portion in the longitudinal direction, respectively, each formed at an area extending along the width direction of the absorbent article.

10. The absorbent article according to claim 9, wherein each of the lattice-shaped front surface compressed parts is provided with intermittent portions at which emboss grooves are placed intermittently at crossing portions of strips of the respective lattice-shaped absorbent body, and is formed in a rhombic lattice-shape in which strips of the respective lattice-shaped absorbent body is inclined with respect to the longitudinal direction and the width direction of the absorbent article.

11. The absorbent article according to claim 10,
wherein the length of each of the intermittent portions is 2 to 5 mm.

12. The absorbent article according to claim 9,
wherein a concave groove is provided at a skin contacting surface at the area corresponding to the body fluid expelling portion along the longitudinal direction, and
wherein the lattice-shaped front surface compressed parts are provided at front and rear areas of the concave groove, respectively.

13. The absorbent article according to claim 1, wherein the absorbent body compressed part is provided so as to overlap a flat portion of the liquid permeable topsheet.

14. The absorbent article according to claim 1, further comprising
another absorbent body compressed part provided from the front surface side of the absorbent body before stacking the liquid permeable topsheet to surround the area corresponding to the body fluid expelling portion,
wherein the front surface compressed part is provided between the absorbent body compressed part and the other absorbent body compressed part.

* * * * *